(12) United States Patent
Sanpitak

(10) Patent No.: US 10,463,252 B2
(45) Date of Patent: Nov. 5, 2019

(54) INTERFACE FOR COMPONENT IDENTIFICATION, COMMUNICATION AND POWER SUPPLY BETWEEN INTERCHANGEABLE SYSTEM COMPONENTS

(75) Inventor: Patanit Sanpitak, Highland Park, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1895 days.

(21) Appl. No.: 11/691,568

(22) Filed: Mar. 27, 2007

(65) Prior Publication Data

US 2008/0237471 A1 Oct. 2, 2008

(51) Int. Cl.

| | |
|---|---|
| G21K 1/02 | (2006.01) |
| A61B 5/00 | (2006.01) |
| A61B 6/03 | (2006.01) |
| A61B 6/00 | (2006.01) |
| A61N 5/10 | (2006.01) |

(52) U.S. Cl.
CPC ............ *A61B 5/0002* (2013.01); *A61B 6/037* (2013.01); *A61B 6/4411* (2013.01); *A61B 6/4494* (2013.01); *A61B 6/56* (2013.01); *A61N 5/10* (2013.01); *A61N 2005/1074* (2013.01)

(58) Field of Classification Search
USPC ...................................................... 250/363.1
See application file for complete search history.

(56) References Cited

U.S. PATENT DOCUMENTS

| | | | |
|---|---|---|---|
| 5,196,682 A * | 3/1993 | Englehardt | 235/454 |
| 5,519,223 A | 5/1996 | Hug et al. | |
| 5,929,598 A * | 7/1999 | Nakama | H02J 7/025 320/108 |
| 6,055,062 A * | 4/2000 | Dina et al. | 358/1.13 |
| 6,417,946 B1 * | 7/2002 | Krieger | H01L 31/0203 257/100 |
| 6,906,328 B2 | 6/2005 | Garrard et al. | |
| 2005/0223148 A1 * | 10/2005 | Kim | 710/260 |
| 2007/0182367 A1 * | 8/2007 | Partovi | H01F 5/003 320/108 |

* cited by examiner

Primary Examiner — David P Porta
Assistant Examiner — Shun Lee

(57) ABSTRACT

A contactless and battery-less interface for component identification and remote sensing is disclosed. The interface includes a near-field electromagnetic coupling for electrical power transfer and a full duplex optical coupling for bi-directional serial communication interface. The interface provides a low-cost and low-power Reduced Instruction Set Computing (RISC) microcontroller with a minimum of components and a low production cost, wherein a communication and power interface can be provided between components such as a gamma camera head and a collimator, without requiring electrical contacts between interface circuit assemblies on the respective parts.

13 Claims, 4 Drawing Sheets

INTERFACE FOR COMPONENT IDENTIFICATION, COMMUNICATION AND POWER SUPPLY BETWEEN INTERCHANGEABLE SYSTEM COMPONENTS

TECHNICAL FIELD

An embodiment of the present invention relates to generally to interfaces for reading identification (ID) and/or other data from interchangeable components in a system, and in particular relates to interfaces for collimator identification and patient contact sensing in nuclear medical imaging apparatus such as a gamma camera. Specifically, an embodiment of the present invention relates to a contactless and battery-less interface that replaces existing collimator ID and patient touch pad interfaces.

BACKGROUND

In nuclear medical applications such as Single Photon Emission Computed Tomography (SPECT) or planar imaging, each detector head of a gamma camera utilizes a collimator which is placed in front of a scintillation crystal that receives incident gamma rays or photons that are emitted from a patient. The purpose of the collimator is to pass through to the scintillation crystal only direct gamma photons that are orthogonal to the crystal surface, and to block all other gamma photons, such as scatter and background photons from impinging on the crystal.

A collimator is typically manufactured from lead material and has an array of parallel apertures or passageways typically arranged in a "honeycomb" configuration. A collimator may weigh from 100 to 250 pounds or more and is mounted on the gamma camera detector so as to cover the surface of the scintillation crystal.

Different collimators have different characteristics that are most suited to the patient study underway. For instance, different collimators are designed for gamma camera studies of different gamma ray energy ranges, or different exposure times. As such, it is common to exchange collimators mounted the detector heads for different types of imaging studies. Each collimator is securely fastened to the detector head during the imaging study to prevent collimator separation from the detector head as the detector heads move or rotate about the patient. An example of a gamma camera apparatus with a detachable and exchangeable collimator is shown in FIG. 1, wherein gamma camera apparatus 20 includes a camera head 28 and an exchangeable collimator 30.

Systems for automated collimator exchange are known in the art. See, e.g., U.S. Pat. No. 5,519,223 issued to Hug et al. and U.S. Pat. No. 6,906,328 issued to Garrard et al., which are incorporated herein by reference in their entireties.

In order to accommodate automated exchange and installation, a collimator typically has mounted on it a printed circuit assembly (PCA) that contains information about the collimator (such as ID, serial number, type, model, size, etc.) stored in a memory chip such as an EPROM, EEPROM, ROM, etc. It is also common for the collimator to have a patient contact or touch pad mounted on the surface that is to face the patient. Such patient touch pad generates a signal when it makes physical contact with a patient, thus alerting the operator of the position of the camera head with respect to the patient and preventing potential harm to the patient by stopping the motion of the camera head.

FIG. 2 is a diagram of a prior art interface assembly for a collimator attached to a gamma camera head, consisting of a collimator PCA 101 and a camera head PCA 107. The collimator PCA 101 contains a memory chip 102 containing collimator-related information, and also is connected to a patient touch pad sensor 105, which is mounted to the collimator surface facing the patient. The PCA 101 includes electrical signal mating contacts 103, which mate with corresponding spring-loaded contacts 109 on the camera head PCA 107. The camera head PCA 107 includes a signal cable 111 that is connected to a data processor such as a microprocessor or microcontroller provided in a housing of the camera apparatus. Typically, the collimator PCA 101 is also powered through the cable 111 and contacts 109.

The conventional collimator interface assembly thus requires electrical contacts to be exposed both on the camera head side as well as the collimator side. These exposed electrical contacts increase the susceptibility of the PCAs 101 and 107 to be damaged by electrostatic discharges (ESD). Additionally, the contacts 103 and 109 are required to be manufactured within tight alignment precision limits in order for the interface assembly to operate properly, and automated exchange systems similarly need to have precise alignment capability in order to properly mount the collimator to the camera head such that the contacts on the collimator PCA 101 properly engage and couple with the contacts on the camera head PCA 107. These requirements increase the manufacturing costs of such devices. Accordingly, there exists a need in the art for improvement in collimator interface design to reduce complexity and cost and susceptibility to damage.

SUMMARY

In accordance with an embodiment, a contactless and battery-less interface for a gamma camera collimator is provided, which combines a near-field electromagnetic coupling for power transfer and a full duplex optical coupling for bidirectional signaling. An embodiment thus eliminates exposed electrical contacts on the circuit assemblies, and eliminates the need for precision tolerances for alignment of contacts between circuit assemblies. In a preferred embodiment, the interface assembly of the invention may be implemented using Reduced Instruction Set Computer (RISC) microcontroller technology having a minimum number of components, which achieves a reduced production cost.

In at least one embodiment, the embodiment provides a contactless interface for providing a power supply and communication between cooperating components of a system, including a first circuit assembly provided on a first system component, including a first optical transmitter/receiver for communicating with another optical receiver/transmitter, wherein said optical receiver/transmitters communicate via infrared, storage medium for storing information pertaining to said first system component, a first inductive trace formed on said first circuit assembly, and a first microcontroller for controlling operation of said transmitter/receiver and controlling reading and writing of information from and to said storage medium; a second circuit assembly provided on a second system component, including a second optical transmitter/receiver for communicating with said first infrared transmitter/receiver via infrared; a second inductive trace formed on said second circuit assembly, for producing a near-field electromagnetic coupling and electrical power transfer with said first inductive trace; and a second microcontroller for controlling operation of said second transmitter/receiver; wherein said first microcontroller reads information from said storage medium and transmits said read information to said second optical transmitter/receiver through said first optical transmitter/receiver.

According to another aspect of the invention, a gamma camera system is provided with an interface between collimator and camera head, which corresponds to the contactless interface described above.

DETAILED DESCRIPTION OF EXEMPLARY EMBODIMENTS

Figure 1:
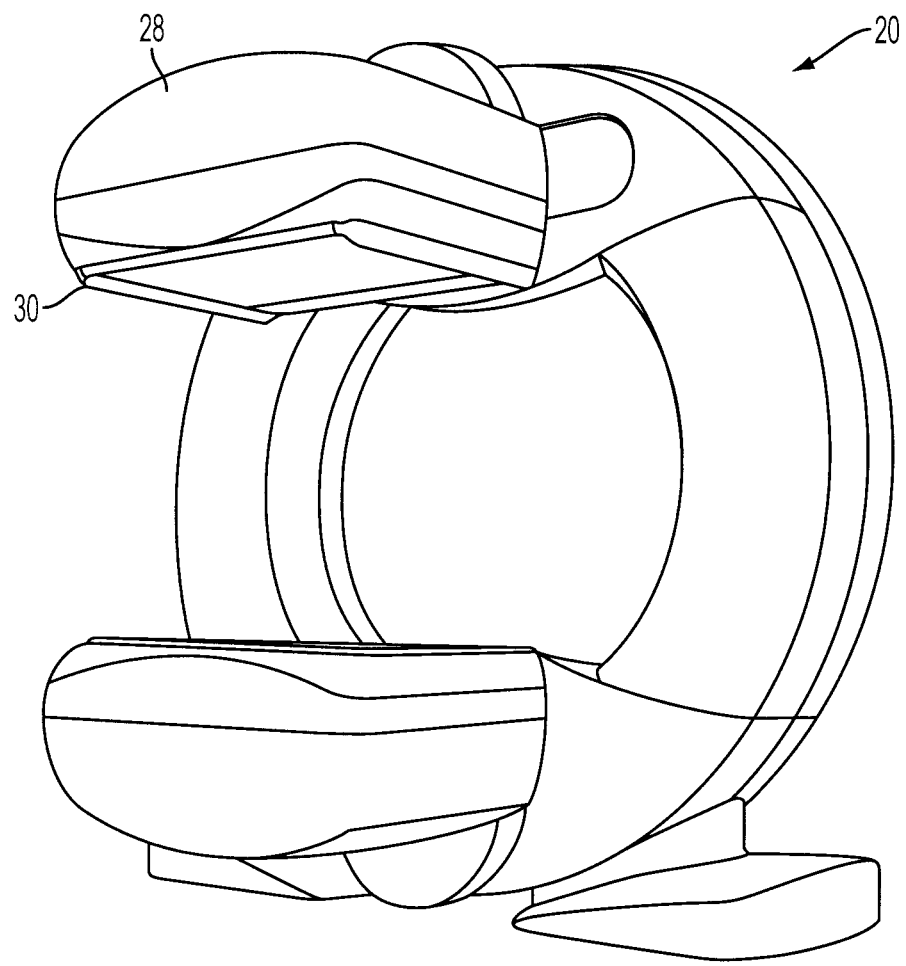
FIG. 1 shows a gamma camera apparatus that is applicable for use with the present invention.
Figure 2:
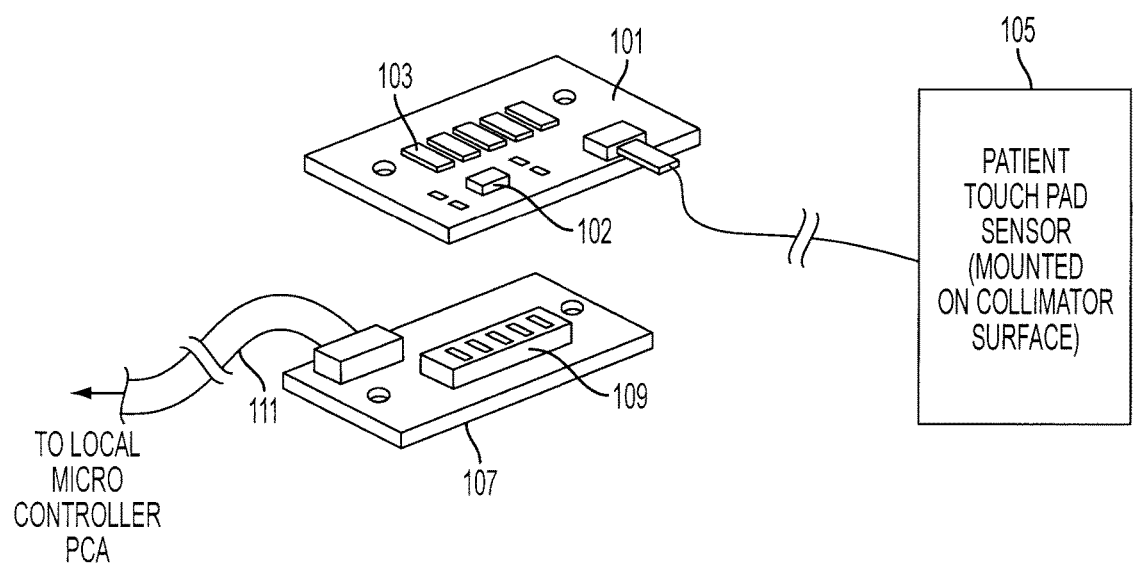
FIG. 2 shows a prior art collimator interface assembly.
Figure 3:
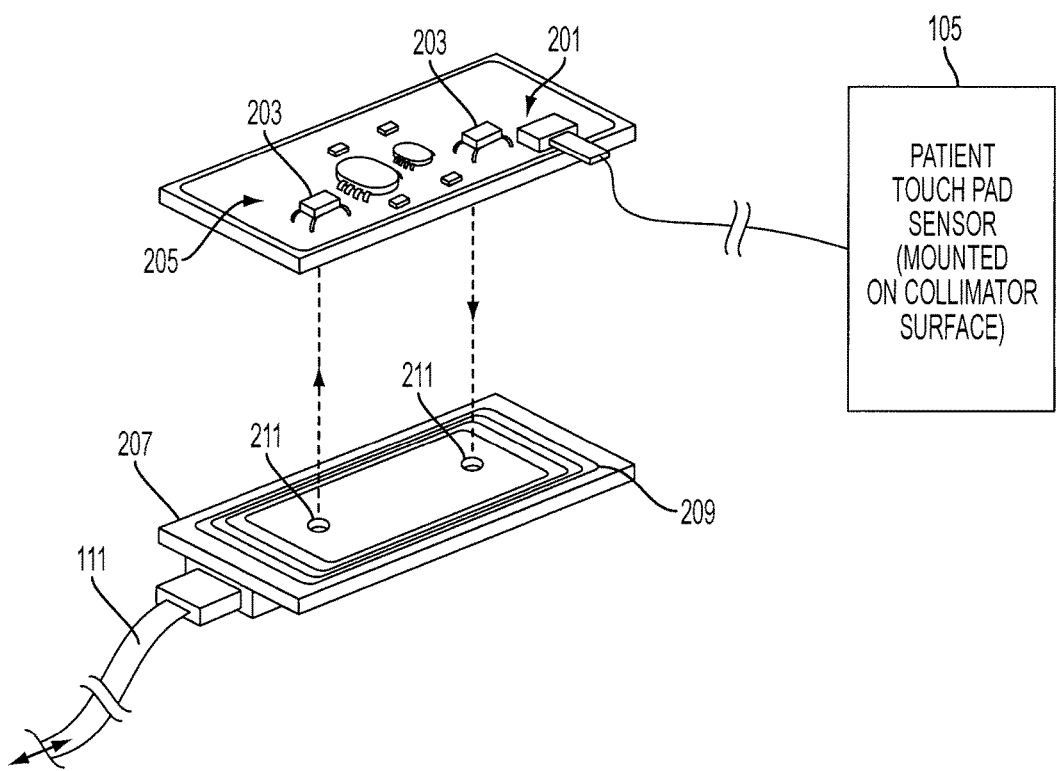
FIG. 3 shows an embodiment of a contactless interface assembly in accordance with an embodiment of the present invention.

FIG. 3 illustrates one embodiment of the invention. A collimator PCA 201 contains an optical transmitter/receiver 203, such as an infrared transmitter/receiver. The transmitter/receiver components are mounted in holes in the PCA board as shown. The PCA 201 further contains an inductive trace or coil 205 formed on the bottom side of the PCA board. Further, as in the prior art, the PCA 201 includes a connection to a patient touch pad sensor 105, which is mounted on the surface of the collimator facing the patient.

The collimator interface assembly in accordance with this embodiment of the invention further includes a camera head PCA 207. PCA 207 contains a corresponding optical transmitter/receiver components 211, such as an infrared transmitter and receiver. Transmitter/receiver components 211 communicate with transmitter/receiver components 203 of collimator PCA 201 via optical signals such as infrared signals. It should be noted that the transmitter/receiver components are not restricted to infrared technology, but can be implemented using any other suitable type of optical or electromagnetic proximity signaling not requiring a hard-wired terminal connection.

PCA 207 further contains an inductive trace or coil 209. Trace 209 is provided with electric current through cable 111 connected to the main processor of the imaging apparatus as explained above. As can be seen in FIG. 3, trace 209 is formed on the top side of PCA 207, facing PCA 201. This is confirmed by FIG. 4, which clearly shows that trace 205 of PCA 201 and trace 209 of PCA 207 face each other. In operation, current flowing through trace 209 in camera head PCA 207 induces through electromagnetic induction a corresponding current to flow through trace 205 in collimator PCA 201, thereby providing electric power for operation of PCA 201. In this way, there is no need to provide a separate power source such as a battery on PCA 201.

The contactless collimator interface in accordance with embodiments provides a number of advantages over the prior art, including: a reduced number of conductors; improved reliability; elimination of precision requirements for alignment of electrical contacts; improved immunity to ESD; ability to add sensing signals for other components/parameters without adding new electrical contacts.

Figure 4:
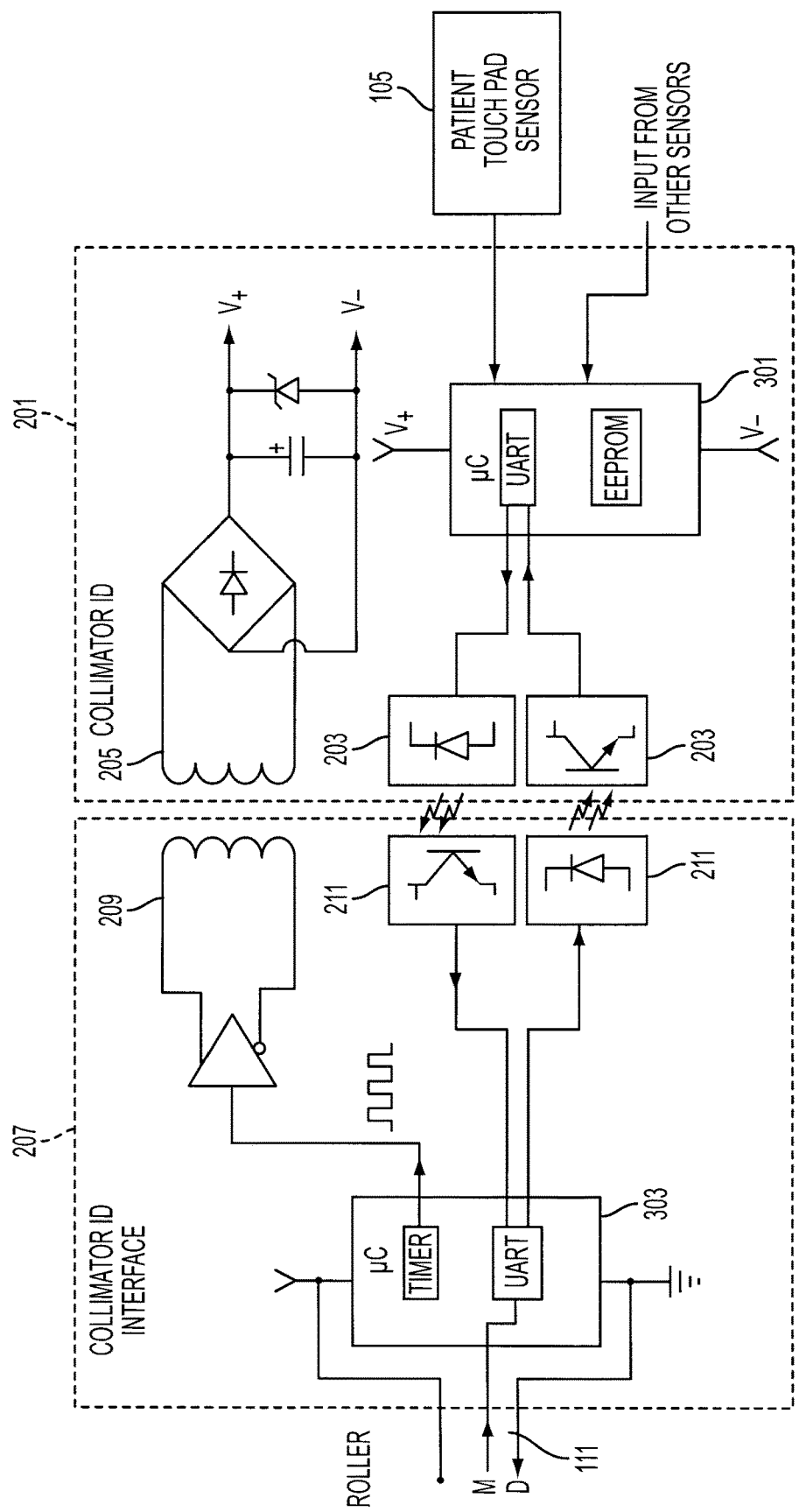
FIG. 4 is a detailed circuit block diagram of an embodiment of the invention as shown in FIG. 3.

FIG. 4 is a detail circuit block diagram showing the detail of a collimator ID interface assembly according to an embodiment. Each PCA includes a microcontroller. Collimator PCA 201 includes a microcontroller (e.g. a RISC microcontroller) 301, and camera head PCA 207 includes a microcontroller (e.g. a RISC microcontroller) 303. Microcontroller 301, as shown, includes a storage medium such as an EEPROM chip, which stores information about the collimator as described above. In operation, the microcontroller 303 on the camera head PCA 207 generates a high frequency square wave signal for driving transmitting component 209 (e.g., coil) (via a differential signal driver), while the receiving component 205 (e.g., coil) of collimator PCA 201 is electromagnetically coupled to the transmitting coil 209. A small amount of electrical energy, sufficient to power collimator PCA 201, is transferred via this near-field electromagnetic coupling. The induced square wave signal on the receiving coil 205 is rectified via a bridge rectifier and filtered, to provide a DC power supply for circuit operation of the collimator PCA 201.

The communication interface between the collimator PCA 201 and the camera head PCA 207 can be implemented with UART (Universal Asynchronous Receiver and Transmitter) technology for each transceiver 203, 211, provided in the respective microcontrollers. In an embodiment, infrared optical transmitters and receivers are used to provide serial communication between the PCAs. The output signal from patient touch pad sensor 105 can be interfaced directly to a built-in analog comparator of the microcontroller 301. The patient touch pad sensor signal can be translated by microcontroller 301 into a serial data signal for input to the microcontroller 303.

Several commercially available microcontrollers are suitable for use with the embodiments. One requirement for microcontroller selection on the collimator side is the ability to operate at low voltage, low power consumption conditions, and having an operating speed high enough for the required UART baud rate. An example of such a microcontroller is the PIC16F688 microcontroller manufactured by Microchip Technology Inc. This chip has a wide operating voltage range of 2.0-5.5V, a calibrated internal clock up to 8 MHz, less than 1 mA operating current at 3.3V, and oscillator frequency of 8 MHz. It also has integrated EEPROM, UART, analog comparator and ADC.

The invention having been thus described, it shall not be deemed to be limited to the illustrative embodiments described above. Instead, a number of other variations and modifications are conceivable and are within the scope of the described embodiments. In particular, while the embodiments have been described in the context of an interchangeable collimator for a nuclear medical imaging system, the embodiments are applicable to other applications where communication and power interfaces are required between interchangeable devices or components.

The invention claimed is:

1. A contactless interface for providing a power supply and communication between a gamma camera system and an interchangeable collimator, comprising:
   a first printed circuit assembly provided on said interchangeable collimator, said first printed circuit assembly including
      a first circuit board,
      a first optical transmitter/receiver mounted on a first side of said first circuit board for communicating with another optical receiver/transmitter,
      a storage medium mounted on said first side of said first circuit board for storing identification information pertaining to said interchangeable collimator,
      a first microcontroller mounted on said first side of said first circuit board for controlling operation of said transmitter/receiver and controlling reading and writing of information from and to said storage medium, and a first inductive trace formed on a side of said first circuit board opposite to said first side of said first circuit board; and a second printed circuit assembly provided on a camera head of said gamma camera system, said second printed circuit assembly including a second circuit board, a second optical transmitter/receiver mounted on a first side of said second circuit board for communicating with said first optical transmitter/receiver, a second microcontroller mounted on said first side of said second circuit board for controlling operation of said second transmitter/receiver, and a second inductive trace formed on a side of said second circuit board opposite to said first side of said second circuit board, for producing a near-field electromagnetic coupling and electrical power transfer with said first inductive trace;

said interchangeable collimator being configured to be securely fastened to said camera head whereby said first microcontroller reads information from said storage medium and transmits said read information to said second optical transmitter/receiver through said first optical transmitter/receiver.

2. The interface of claim 1, wherein said second printed circuit assembly further includes a power and signal cable operatively coupled to a main controller of said system.

3. The interface of claim 1, wherein said first printed circuit assembly further includes a connection to a remote sensor.

4. The interface of claim 1, wherein said first and second printed circuit assemblies each further comprise a universal asynchronous receiver and transmitter (UART) for infrared communication therebetween.

5. The interface of claim 1, wherein said storage medium comprises an EEPROM.

6. The interface of claim 1, wherein said first circuit assembly further comprises a rectifier for processing a square wave signal from said second inductive trace.

7. The interface of claim 1, wherein said first printed circuit assembly further includes a connection to a patient touch pad sensor mounted on a surface of said collimator.

8. The interface of claim 1, wherein a serial data connection is established between said first and second transmitter/receivers for communicating data between said first and second microcontrollers.

9. A gamma camera system, comprising:
a camera head;
a collimator interchangeably mounted to said camera head;
a first printed circuit assembly mounted on said collimator, said first printed circuit assembly including
a first circuit board,
a first optical transmitter/receiver, mounted on a first side of said first circuit board, for communicating with another optical receiver/transmitter,
a storage medium, mounted on a first side of said first circuit board, for storing identification information pertaining to said collimator,
a first microcontroller, mounted on a first side of said first circuit board, for controlling operation of said transmitter/receiver and controlling reading and writing of information from and to said storage medium, and
a first inductive trace formed on a side of said first circuit board opposite to said first side of said first circuit board; and
a second printed circuit assembly mounted on said camera head, said second printed circuit assembly including
a second circuit board,
a second optical transmitter/receiver, mounted on a first side of said second circuit board, for communicating with said first optical transmitter/receiver,
a second microcontroller, mounted on a first side of said second circuit board, for controlling operation of said second transmitter/receiver, and
a second inductive trace formed on a side of said second circuit board opposite to said first side of said second circuit board, for producing a near-field electromagnetic coupling and electrical power transfer with said first inductive trace;
wherein said first microcontroller reads information from said storage medium and transmits said read information to said second optical transmitter/receiver through said first optical transmitter/receiver.

10. A gamma camera system as set forth in claim 9, wherein said collimator is removable and exchangeable with other collimators to be mounted to said camera head.

11. A gamma camera system as set forth in claim 9, further comprising a patient touch pad sensor mounted to a surface of said collimator facing a patient undergoing imaging by said gamma camera system, wherein said first circuit assembly includes a connection to receive a signal from said patient touch pad sensor.

12. A gamma camera system as set forth in claim 9, wherein said first and second optical transmitter/receivers comprise infrared transmitter/receivers.

13. A gamma camera system as set forth in claim 9, wherein said first and second optical transmitter/receivers comprise universal asynchronous receiver transmitters (UARTs).

* * * * *